(12) United States Patent
Pond, Jr. et al.

(10) Patent No.: US 7,491,208 B2
(45) Date of Patent: Feb. 17, 2009

(54) INSTRUMENT AND METHOD FOR GUIDING SURGICAL IMPLANTS AND INSTRUMENTS DURING SURGERY

(75) Inventors: John D. Pond, Jr., Germantown, TN (US); Anthony J. Melkent, Memphis, TN (US); Aurelien Bruneau, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 181 days.

(21) Appl. No.: 11/117,034

(22) Filed: Apr. 28, 2005

(65) Prior Publication Data

US 2006/0247658 A1  Nov. 2, 2006

(51) Int. Cl.
*A61B 17/56* (2006.01)
(52) U.S. Cl. .................................................. 606/104
(58) Field of Classification Search ................. 606/61, 606/86, 99, 104, 246, 277, 279
See application file for complete search history.

(56) References Cited

U.S. PATENT DOCUMENTS

| | | | |
|---|---|---|---|
| 2,338,159 A | 1/1944 | Appleton | |
| 4,246,660 A | 1/1981 | Wevers | |
| 4,335,715 A | 6/1982 | Kirkley | |
| 4,411,259 A * | 10/1983 | Drummond | 606/61 |
| 4,545,374 A | 10/1985 | Jacobson | |
| 4,573,448 A | 3/1986 | Kambin | |
| 4,722,331 A | 2/1988 | Fox | |
| 4,883,048 A | 11/1989 | Purnell et al. | |
| 4,896,661 A | 1/1990 | Bogert et al. | |
| 4,955,885 A | 9/1990 | Meyers | |
| 5,020,519 A * | 6/1991 | Hayes et al. | 606/237 |
| 5,163,940 A | 11/1992 | Bourque et al. | |
| 5,242,443 A | 9/1993 | Kambin | |
| 5,242,444 A | 9/1993 | MacMillan | |
| 5,281,223 A | 1/1994 | Ray | |
| 5,334,205 A | 8/1994 | Cain | |
| 5,383,454 A | 1/1995 | Bucholz | |
| 5,437,667 A | 8/1995 | Papierski et al. | |
| 5,569,248 A | 10/1996 | Mathews | |
| 5,571,109 A * | 11/1996 | Bertagnoli | 606/61 |
| 5,591,165 A | 1/1997 | Jackson | |
| 5,591,167 A | 1/1997 | Laurain et al. | |
| 5,601,562 A | 2/1997 | Wolf et al. | |
| 5,613,971 A | 3/1997 | Lower et al. | |
| 5,643,273 A | 7/1997 | Clark | |
| 5,681,320 A | 10/1997 | McGuire | |
| 5,704,937 A | 1/1998 | Martin | |
| 5,720,751 A | 2/1998 | Jackson | |
| 5,725,532 A | 3/1998 | Shoemaker | |

(Continued)

FOREIGN PATENT DOCUMENTS

DE  42 38 339 A1  5/1994

(Continued)

*Primary Examiner*—Eduardo C Robert
*Assistant Examiner*—Michael J Araj
(74) *Attorney, Agent, or Firm*—Krieg Devault (57) ABSTRACT

An apparatus is provided for guiding a surgical implant to a bone anchor during surgery. The apparatus includes a bone anchor extender releasably attachable to the bone anchor wherein the bone anchor extender clips onto a head portion of the bone anchor to assist in guiding the surgical implant to the bone anchor.

28 Claims, 10 Drawing Sheets

U.S. PATENT DOCUMENTS

| | | | |
|---|---|---|---|
| 5,735,857 A | 4/1998 | Lane | |
| 5,741,266 A | 4/1998 | Moran et al. | |
| 5,752,962 A | 5/1998 | D'Urso | |
| 5,772,594 A | 6/1998 | Barrick | |
| 5,851,183 A | 12/1998 | Bucholz | |
| 5,871,445 A | 2/1999 | Bucholz | |
| 5,891,034 A | 4/1999 | Bucholz | |
| 5,891,150 A | 4/1999 | Chan | |
| 5,891,158 A | 4/1999 | Manwaring et al. | |
| 5,910,141 A | 6/1999 | Morrison et al. | |
| 6,036,692 A * | 3/2000 | Burel et al. | 606/61 |
| 6,099,528 A | 8/2000 | Saurat | |
| 6,123,707 A | 9/2000 | Wagner | |
| 6,183,472 B1 * | 2/2001 | Lutz | 606/61 |
| 6,226,548 B1 | 5/2001 | Foley et al. | |
| 6,235,028 B1 | 5/2001 | Brumfield et al. | |
| 6,440,133 B1 | 8/2002 | Beale et al. | |
| 6,530,929 B1 | 3/2003 | Foley et al. | |
| 6,613,091 B1 | 9/2003 | Zdeblick et al. | |
| 7,004,947 B2 | 2/2006 | Shluzas et al. | |
| 2002/0020255 A1 | 2/2002 | Simon et al. | |
| 2002/0045904 A1 | 4/2002 | Fuss et al. | |
| 2002/0161368 A1 | 10/2002 | Foley et al. | |
| 2003/0009168 A1 | 1/2003 | Beale et al. | |
| 2003/0028195 A1 | 2/2003 | Bette | |
| 2003/0060826 A1 * | 3/2003 | Foley et al. | 606/61 |
| 2003/0073998 A1 | 4/2003 | Pagliuca et al. | |
| 2003/0149438 A1 * | 8/2003 | Nichols et al. | 606/99 |
| 2003/0225408 A1 * | 12/2003 | Nichols et al. | 606/61 |
| 2004/0039384 A1 | 2/2004 | Boehm, Jr. et al. | |
| 2004/0138662 A1 | 7/2004 | Landry et al. | |
| 2004/0143265 A1 | 7/2004 | Landry et al. | |
| 2004/0147928 A1 | 7/2004 | Landry et al. | |
| 2004/0147936 A1 | 7/2004 | Rosenberg et al. | |
| 2004/0147937 A1 * | 7/2004 | Dunbar et al. | 606/99 |
| 2005/0043742 A1 | 2/2005 | Bruneau et al. | |
| 2005/0149053 A1 * | 7/2005 | Varieur et al. | 606/104 |

FOREIGN PATENT DOCUMENTS

| | | |
|---|---|---|
| DE | 10 2004 012 417 A1 | 4/2005 |
| EP | 1 374 786 A2 | 1/2004 |
| EP | 1 574 175 A1 | 9/2005 |
| WO | WO 97/38639 | 10/1997 |
| WO | WO 99/26549 | 6/1999 |
| WO | WO 03/028566 A1 | 4/2003 |
| WO | WO 2005/072081 | 8/2005 |

* cited by examiner

INSTRUMENT AND METHOD FOR GUIDING SURGICAL IMPLANTS AND INSTRUMENTS DURING SURGERY

BACKGROUND OF THE INVENTION

The present invention relates to surgical devices and methods and more particularly, but not exclusively, to fixation element extension devices for use during surgical procedures.

Several surgical procedures utilize fixation elements that can be secured to bone or bony structures. These fixation elements can be used to apply stabilizing or corrective forces to the bone or bony structures. A wide variety of fixation elements are provided that are specifically designed to connect to or engage in various bones or bony structures. For example, such fixation elements can include bone screws, posts or spikes that can be anchored into various bones or bony structures. In addition, another fixation element is a hook that is configured to engage the laminae of the vertebra. More specifically, even other fixation elements include spinal screws or bolts having threaded sections that are configured to be anchored in vertebral bone. With reference to spinal surgery, the spinal screws are typically used in conjunction with other implant components used to stabilize the vertebra. These other implant components can include, for example, a stabilization device, such as, a spinal rod or plate. Typically, the spinal screws include a connector portion that is adapted to engage the stabilization device. The connector portion usually has a first opening adapted to receive and engage an upper portion of the spinal screw, and a second opening adapted to receive and engage the stabilization device. The second opening is also configured to engage a securing member that connects the stabilization device to the spinal screw.

Assembly, delivery and manipulation of the implant components described hereinabove can be awkward or cumbersome due to the limited amount of space available to manipulate the implant components and the required surgical instruments. Additionally, if the second opening of the connector portion is not properly aligned, difficulty can be encountered inserting various implant components to the surgical site. Further, if the openings in the connector portions are not aligned with the stabilization devices, forces may need to be applied to stress the stabilization devices to achieve proper alignment with the connector portions. Also, the assembly and manipulation of multiple implant components within the surgical site can be tedious and time consuming, thus, prolonging the surgical procedure and increasing the risks associated therewith. In addition, there are risks associated with mishandling the implant components during delivery to the surgical site, and, if guiding devices are not used, the implant components can be dropped or improperly located within the surgical site.

Therefore, there is a desire in the industry to provide surgical instrumentation and methods for advancing and guiding implant components from outside the body to a location adjacent to a surgical site. There is, further, a desire for instrumentation and method for advancing and guiding implant components that also aligns the connector portions of the fixation elements to readily and easily accept a stabilizing device. Also, there is a desire for instrumentation and methods for advancing and guiding implant components and aligning connection portions that quickly and easily attach to and release from the fixation elements without the exertion of undesirable forces to the surgical site.

BRIEF SUMMARY OF THE INVENTION

In one embodiment, a device is provided for guiding surgical implants to a bone anchor during surgery. The device includes a first bone anchor extender releasably attachable to a first portion of a head portion of the bone anchor. The first bone anchor extender includes a first clip for receiving and releasably attaching to the first portion of the head portion of the bone anchor, and a first extension portion extending longitudinally from the first clip to a position above said head portion of the bone anchor when the first clip is releasably attached to the head portion of the bone anchor. A second bone anchor extender is provided and is releasably attachable to a second portion of the head portion of the bone anchor. The second bone anchor extender includes a second clip for receiving and releasably attaching to the second portion of the head portion of the bone anchor, and a second extension portion extending longitudinally from the second clip to a position above the head portion of the bone anchor when the second clip is releasably attached to the head portion of the bone anchor. The first and second bone anchor extenders are used to assist in guiding the surgical implant to the bone anchor.

In another embodiment, a device is provided for removing a releasable bone anchor extender from a bone anchor. The device includes a handle, a shaft connected to the handle and a head connected to the shaft. The head includes a wedge portion that is adapted to be placed between the bone anchor extender and the bone anchor for releasing the bone anchor extender from the bone anchor when a force is applied to the handle.

In even another embodiment, a system is provided for securing a bone anchor into a boney elements. The system includes a bone anchor inserter having a driver that mates with a head of a bone anchor. The driver is adapted to secure the bone anchor into the boney element. The bone anchor inserter further includes an outer surface having a retainer. A bone anchor extender can be releasably attached to the bone anchor. The bone anchor extender has an elongated portion wherein when the elongated portion is inserted in the retainer of the bone anchor inserter the bone anchor is held in a position for securing the bone anchor into the boney element.

In yet another embodiment, a system is provided for securing a bone anchor to a boney element and guiding an implant to the bone anchor. The system includes a bone anchor extender releasably attachable to a portion of a head of the bone anchor. The bone anchor extender includes a clip for receiving and releasably attaching to the portion of the head of the bone anchor and an extension portion extending longitudinally from the clip to a position above the head of the bone anchor when the clip is releasably attached to the head of the bone anchor. A bone anchor inserter is provided and includes a driver that mates with a portion of said bone anchor. The driver is adapted to secure the bone anchor into the boney element. The bone anchor inserter further includes an outer surface having a retainer. When the elongated portion is inserted in the retainer of the bone anchor inserter, the bone anchor is held in a position for securing the bone anchor into the boney element. A bone anchor extender remover is provided that includes a handle connected to a shaft. A head is also connected to the shaft, and the head includes a wedge portion adapted to be placed between the bone anchor extender and the bone anchor for releasing the bone anchor extender from the bone anchor when a force is applied to the handle.

In even another embodiment, a method for guiding an implant to a bone anchor is provided. The method includes accessing a vertebral body of the spinal column and implanting a bone anchor in the vertebral body. First and second bone anchor extender are releasably attached to a head portion of the bone anchor. Each of the bone anchor extenders comprise an elongated portion extending above the bone anchor. The elongated members define a pathway for the implant. The implant is guided along the pathway to the bone anchor. The implant is secured within the head portion of the bone anchor. The bone anchor extenders are removed from said head portion of said bone anchor.

DETAILED DESCRIPTION OF THE INVENTION

For the purpose of promoting an understanding of the principles of the invention, reference will be made to the embodiments illustrated in the drawings and specific language will be used to describe the same. It will nevertheless be understood that no limitation of the scope of the invention is hereby intended nor should any such limitation be construed. Any such alterations and further modifications in the illustrated devices and described methods, and any such further applications of the principles of the invention as illustrated herein are contemplated as would normally occur to one skilled in the art to which the invention relates.

Figures 1, 2:
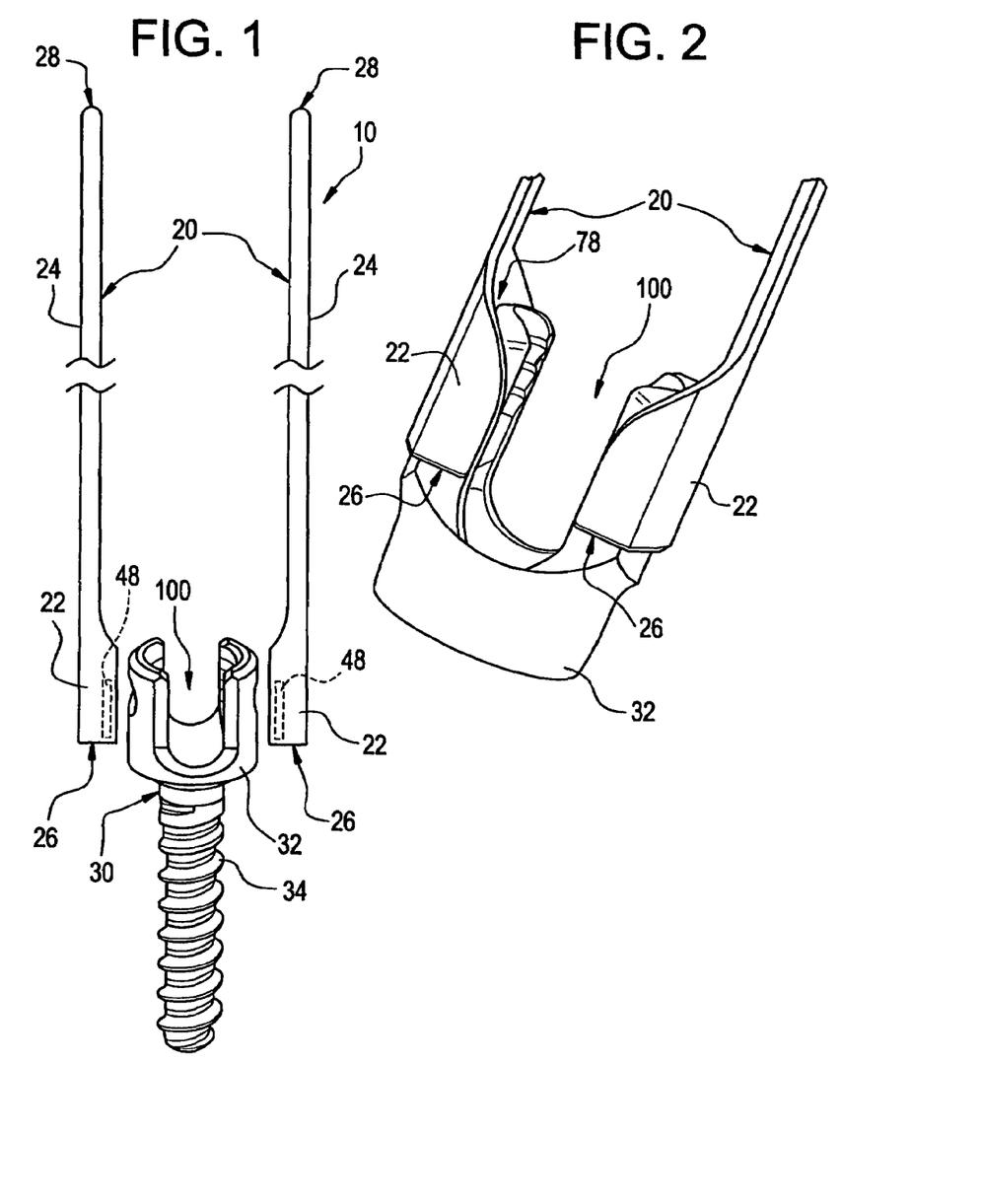
FIG. 1 is a perspective view of one embodiment of extenders and a bone anchor.
FIG. 2 is a perspective view of one embodiment of extenders attached to a head of a bone anchor.

As shown in FIG. 1, one embodiment of the surgical system 10 includes extenders 20 that can be releasably attached to a bone anchor 30. In one embodiment, the mechanism for releasably attaching the extenders 20 to the bone anchor 30 includes clipping the extenders 20 to the bone anchor 30. Each of the extenders 20 includes a clip 22 located at a proximal end 26 of the extender 20. It should be appreciated that the invention encompasses any mechanism that can releasably attach the extenders 20 to the bone anchor 30. In addition, each of the extenders 20 includes an elongated portion 24 that longitudinally extends from the clip 22 to a distal end 28 of the extender 20. As further shown in FIG. 1, the bone anchor 30 comprises a head 32 and a threaded portion 34. It should also be appreciated that the bone anchor 30 can comprise, for example, a screw, a multi-axial screw, a staple or a spike. As further shown in FIG. 2, the extenders 20 are releasably attached to the head 32 of the bone anchor 30. In this embodiment, the clip 22 of each of the extenders 20 is releasably attached to a portion of the head 32 of the bone anchor 30. In releasably attaching the clip 22 to the portion of the head 32, the proximal end 26 of the extender 20 is positioned near the portion of the head 32 and a force from a user's hand or an appropriate tool is applied to the clip 22 to snap the clip onto the portion of the head 32. It should further be appreciated that although the extenders 20 are shown in FIG. 1 to comprise two separate extenders 20, the extenders 20 could be connected as a single unit at any portion along the extender 20. In addition, it should also be appreciated that in an embodiment where the extenders 20 comprise two separate extenders 20, one extender 20 can be clipped or attached to the bone anchor 30. In this embodiment, the single extender 20 can be used to guide an implant 110 (FIG. 13) to the bone anchor 30.

Figure 3:
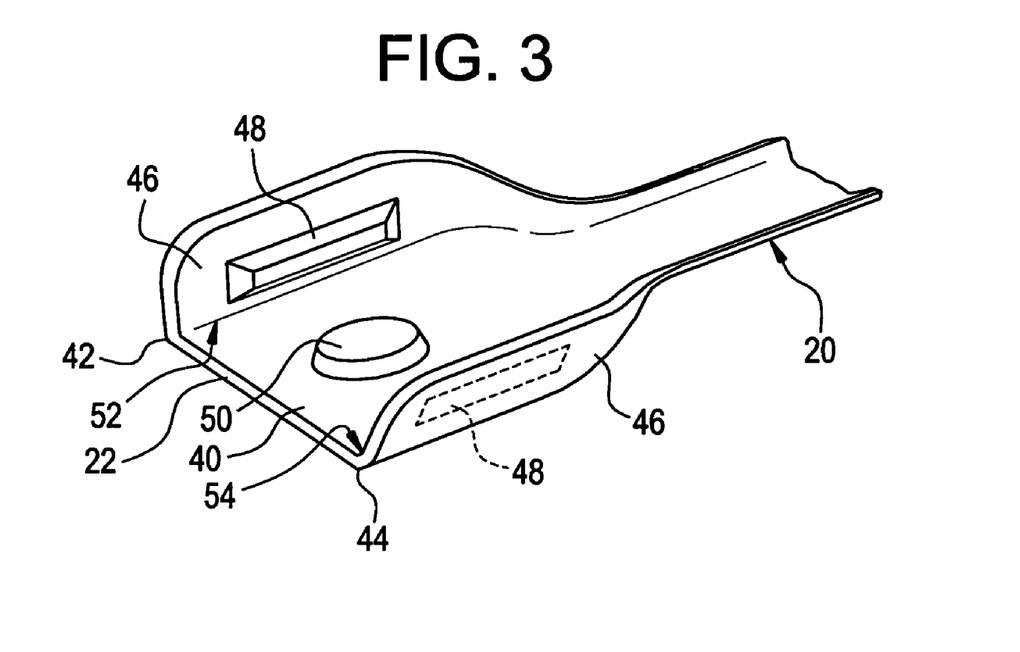
FIG. 3 is a perspective view of one embodiment of a clip of an extender.
Figure 4:
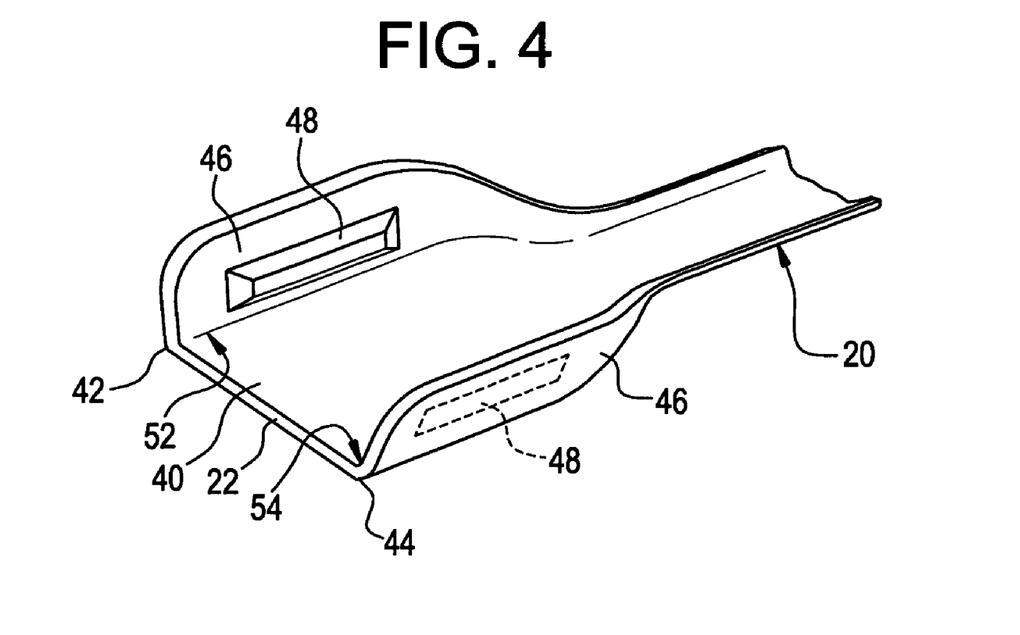
FIG. 4 is a perspective view on another embodiment of a clip of an extender.

In the embodiment shown in FIGS. 3 and 4, the clip 22 of the extender 20 includes a medial portion 40 having a first end 42 and a second end 44. Side portions 46 extend from the medial portion 40 at both the first end 42 and the second end 44. In one embodiment, the side portions 46 extend perpendicularly or at a ninety (90) degree angle from the medial portion 40. In another embodiment, the side portions 46 extend substantially perpendicularly from the medial portion 40. Each side portion 46 includes a raised tab 48. Each raised tab 48 is positioned a predetermined distance from each of the first interface 52 and the second interface 54 between the medial portion 40 and each of the side portions 46. In one embodiment, each of raised tabs 48 is located less than 2 millimeters (mm) from the respective first interface 52 or the second interface 54. In another embodiment, the raised tabs 48 are about 1.35 mm in length. As shown in FIG. 3, one embodiment of the extender 20 includes a bumper 50 positioned on the medial portion 40. In this embodiment, the bumper 50 may be used to ensure proper spacing between the head 32 of the bone anchor 30 and the extender 20 when the extender 20 is attached to the bone anchor 30.

Figure 5:
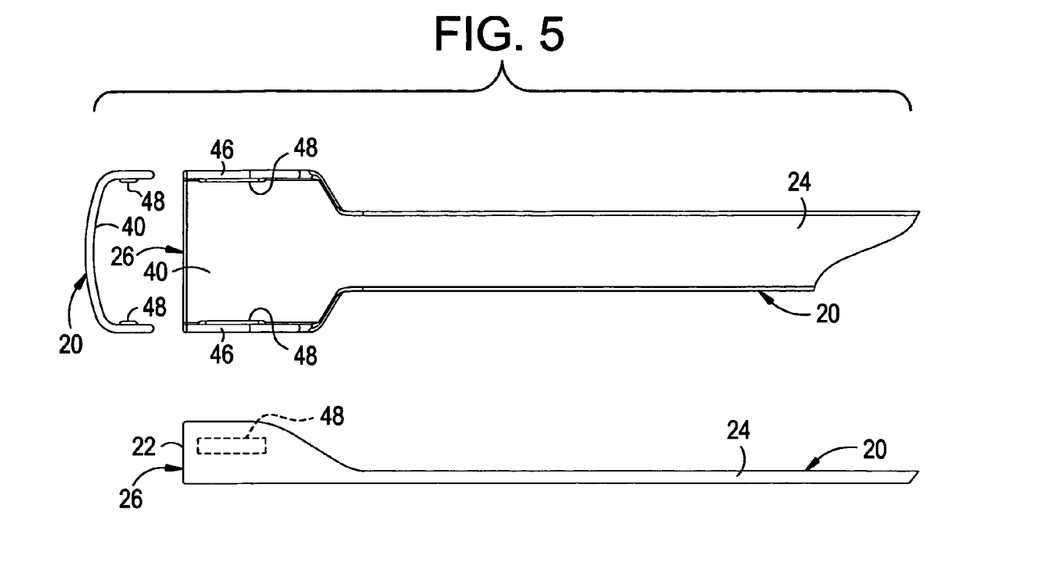
FIG. 5 is a front, top and cross-sectional views of one embodiment of an extender.
Figure 6:
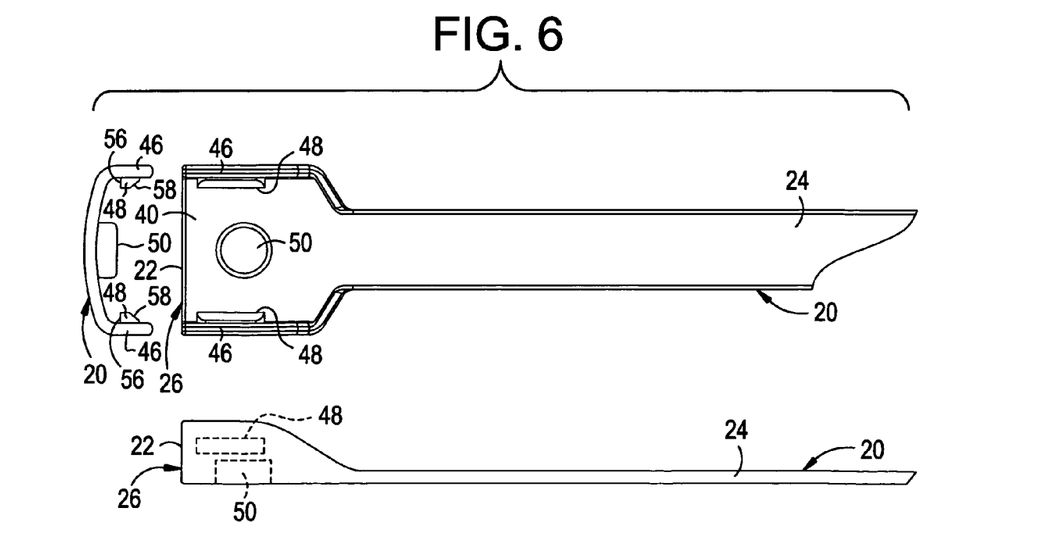
FIG. 6 is a front, top and cross-sectional view of another embodiment of an extender.

As further shown in FIGS. 5 and 6, the extender 20 is shown comprising clip 22 and elongated portion 24. As described above, the extender 20 includes raised tab portions 48 on side portions 46. As shown in FIGS. 5 and 6, in one embodiment, the medial portion 40 is contoured. In another embodiment, the contour of the medial portion 40 comprises an arc. In even another embodiment, the contour of the medial portion 40 is contoured to correspondingly mate with a portion of the head 32 of the bone anchor 30. In yet another embodiment, the elongated portion 24 can be substantially flat. As shown in FIG. 6, the raised tab 48 includes a retention edge 56 and an angled face 58. In this embodiment, the retention edge 56 is positioned opposite from the angled face 58, and the retention edge 56 is positioned closer to the medial portion 40 than the angled face 58. It should be appreciated that, in this embodiment, the angled face 58 and the retention edge 56 assist in releasably attaching the extender 20 to the bone anchor 30. Further in this regard, when the extender 20 is being releasably attached to the bone anchor 30, a portion of the head 32 of the bone anchor 30 is placed in contact with the clip 22 of the extender 20. The angled face 58 contacts the portion of the head 32 of the bone anchor 30 as a force is applied to the clip 22 of the extender 20 to releasably attach the extender 20 the bone anchor 30. The angled face 58 assists in guiding the extender 20 onto the head 32 of the bone anchor 30. As a force is being applied to the clip 22, the portion of the head 32 of the bone anchor 30 is moved along the angled face 58 until it is positioned and captured in the retention edge 56. In one embodiment, the extender 20 including its various portions, such as, the elongated portion, 24, clip 22, medial portion 40 and side portion 46, comprises a thickness that allows the portions of the extender 20 to elastically deform and/or bend and then revert back to their original shape. It should be appreciated that the clip 22 of the extender 20 is releasably attached to the bone anchor 30 tightly enough to allow the elongated portion 24 to be elastically deformed or bent without the clip 22 releasing from bone anchor 20. In one embodiment, the extender 20 has a thickness of 1 to 10 millimeters (mm). In another embodiment, the extender 20 has a thickness of 1 to 5 mm. In even another embodiments, the extender 20 has a thickness of 1, 2, 3, 4, 5, 6, 7, 8, 9 or 10 mm. In yet another embodiment, the extender 20 has a thickness of less than 1 mm. In another embodiment, the extender 20 has a thickness of greater than 10 mm. In one embodiment, the clip 22 is about 11 mm in length and the length of the entire extender 20 is about 154 mm and the width of the elongated portion 24 is about 5 mm. It should be appreciated that, in one embodiment, the extender 20 can be formed from a single piece of material. In another embodiment, the raised tab 48 and the bumper can be integrally formed with the clip 22. In one embodiment, the extender 20 can be composed of a bio-compatible material. In another embodiment, the extender 20 can be composed of a material, such as, titanium, stainless steel or a steel alloy. In even another embodiment, the extender 20 can be composed of a polymeric material. In yet another embodiment, the extender 20 can comprise a clip 22 that is composed of a polymeric material and an elongated portion 24 that is composed of a metallic material. Conversely, the extender 20 can comprise a clip 22 that is composed of a metallic material and an elongated portion 24 that is composed of a polymeric material. In FIG. 6, the raised tab 48 having the retention edge 56 and the angled face 58 is shown with an extender 20 having a bumper 50. However, it should be appreciated that, in other embodiments, the raised tab 48 having the retention edge 56 and the angled face 58 can be used with an extender 20 that does not incorporate a bumper 50.

Figures 7, 8:
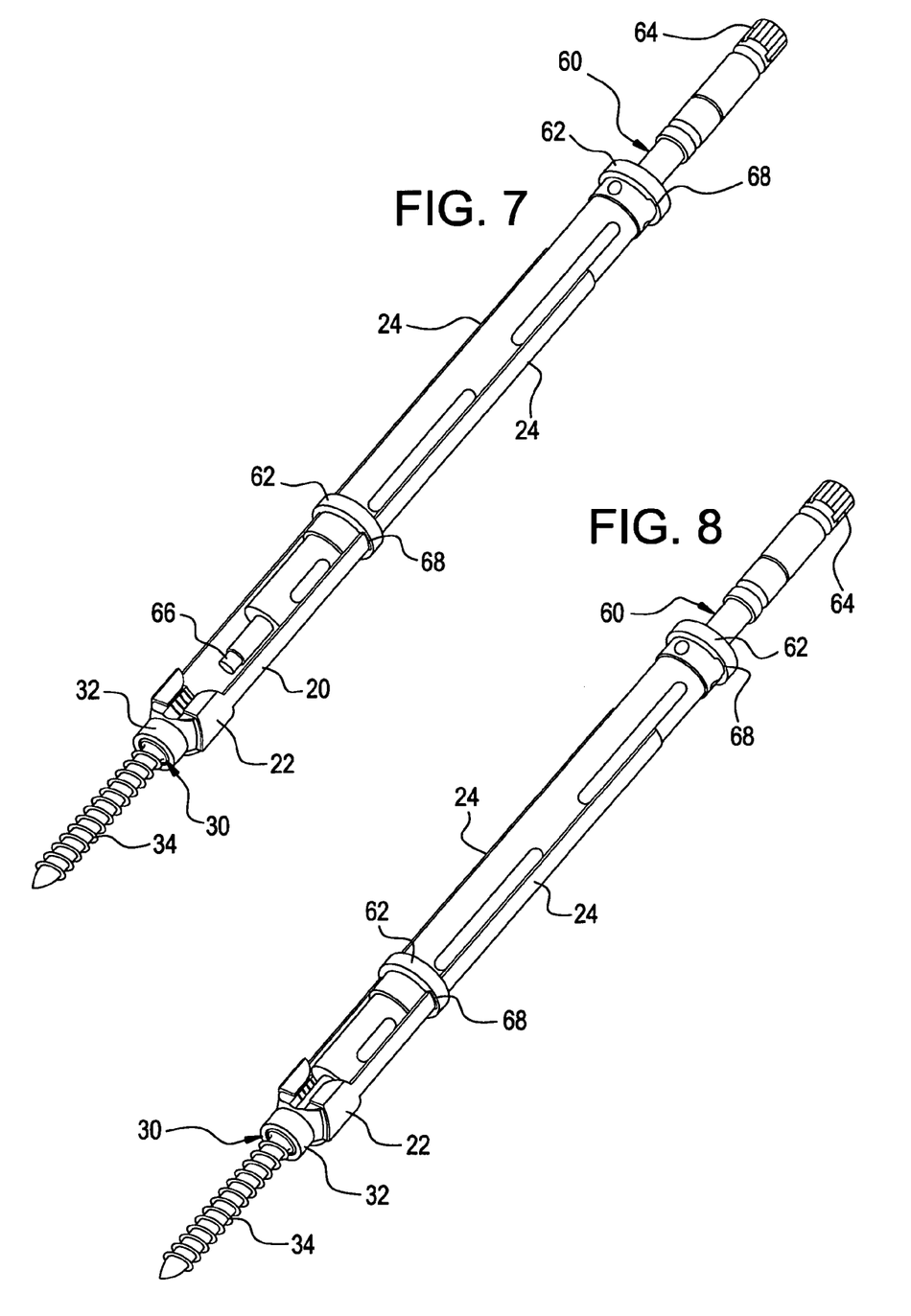
FIG. 7 is a perspective view of one embodiment of a driver, extenders and bone anchor.
FIG. 8 is a perspective of one embodiment of a driver engaged with extenders and a bone anchor.
Figures 9, 10:
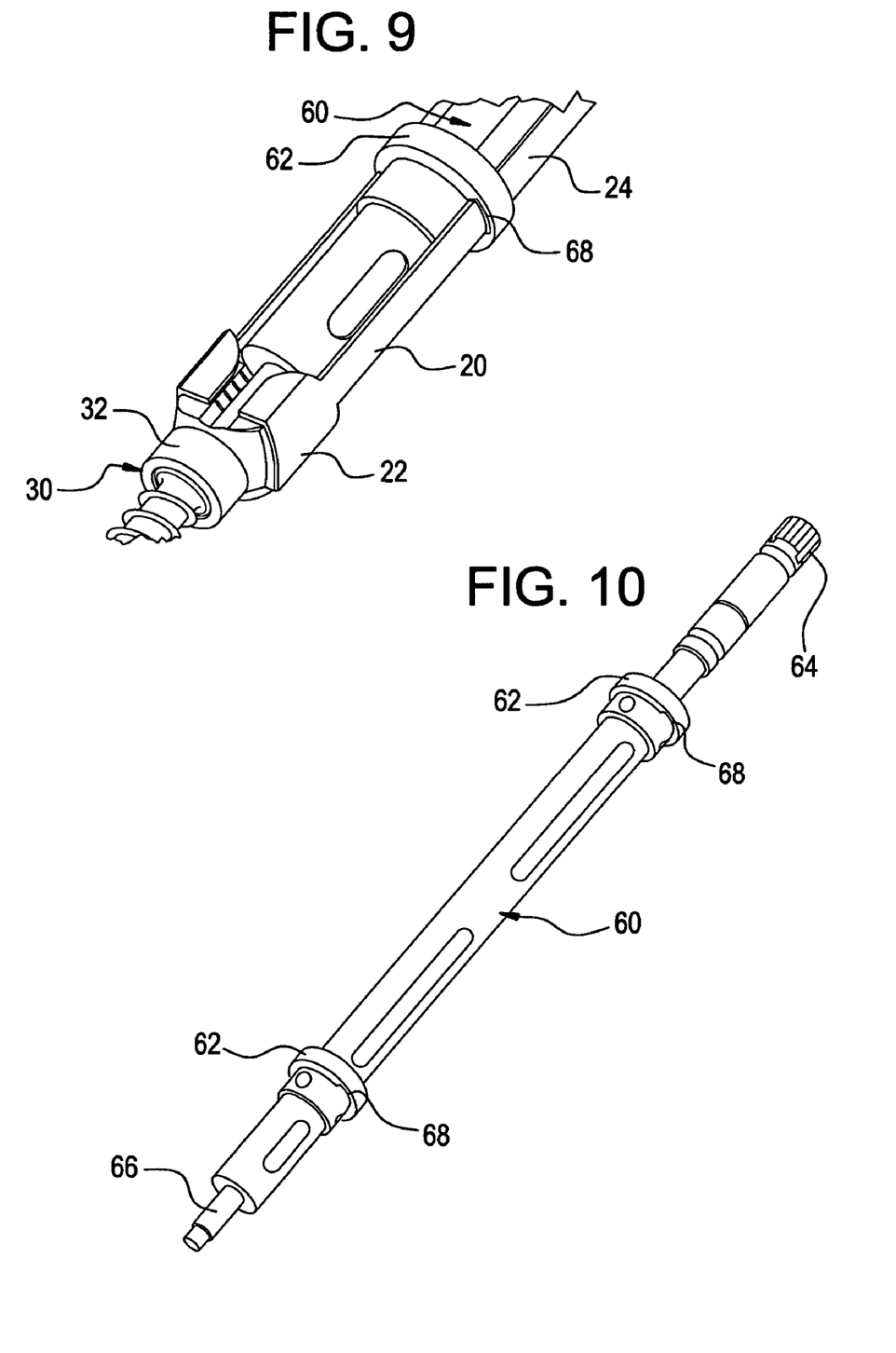
FIG. 9 is a close-up perspective view of one embodiment of a driver engaged with extenders and a bone anchor.
FIG. 10 is a perspective view of one embodiment of a driver.
Figure 13:
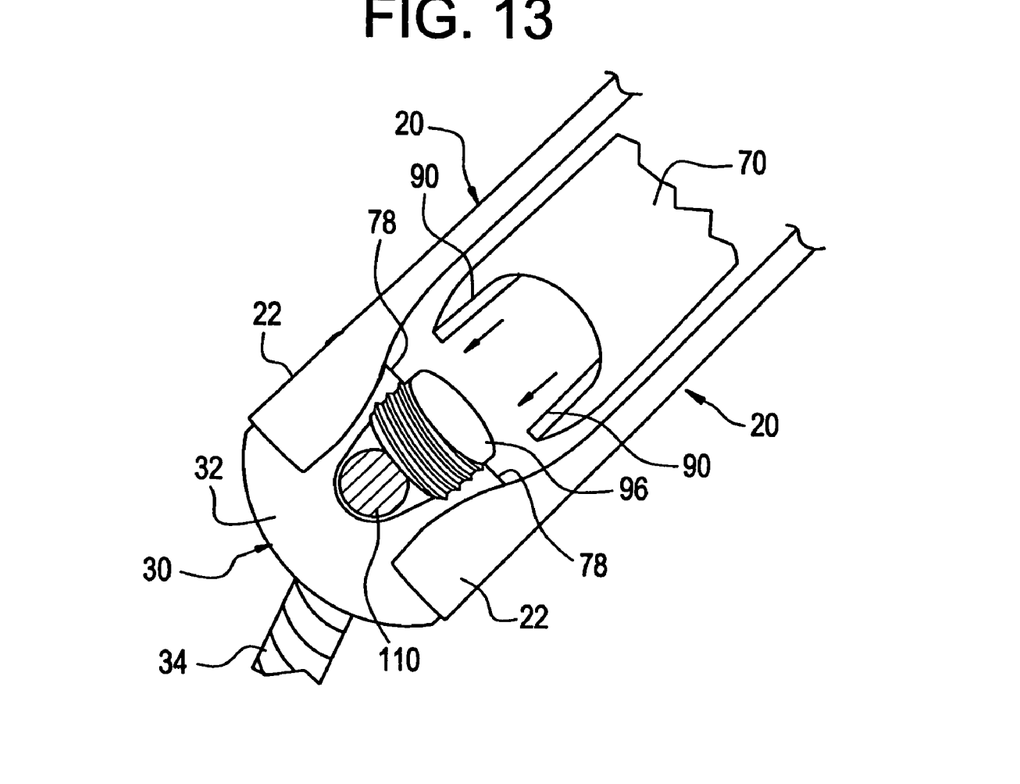
FIG. 13 is a perspective view of another embodiment of an extender remover tool, extender and a bone anchor.
Figure 16:
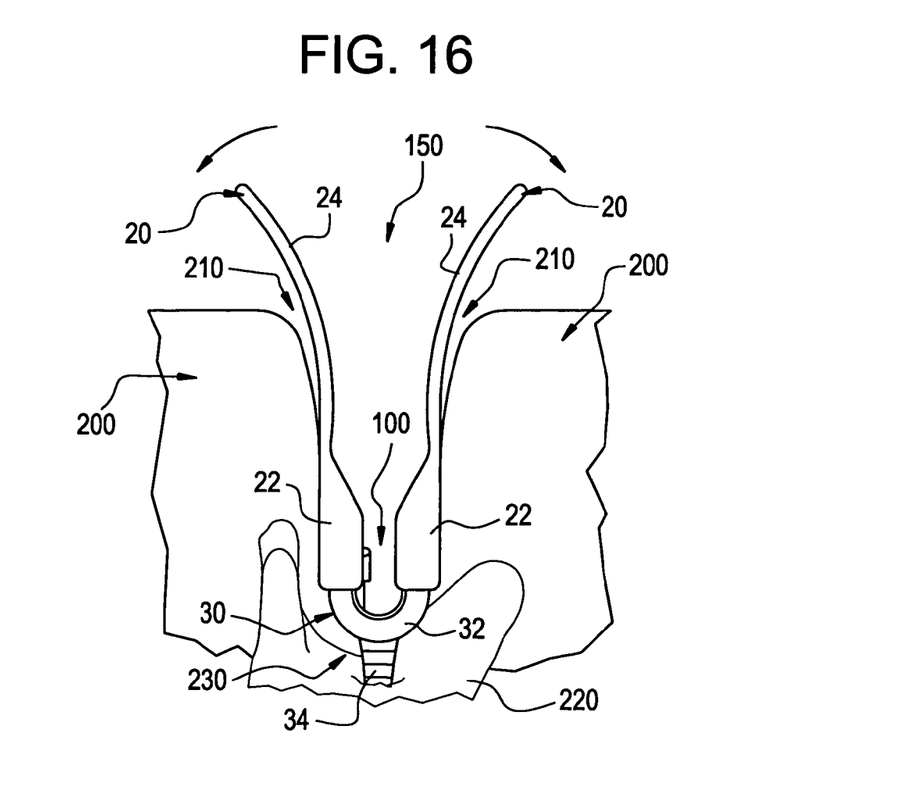
FIG. 16 is perspective view of one embodiment of extenders and a bone anchor used in a surgical procedure.
Figure 18:
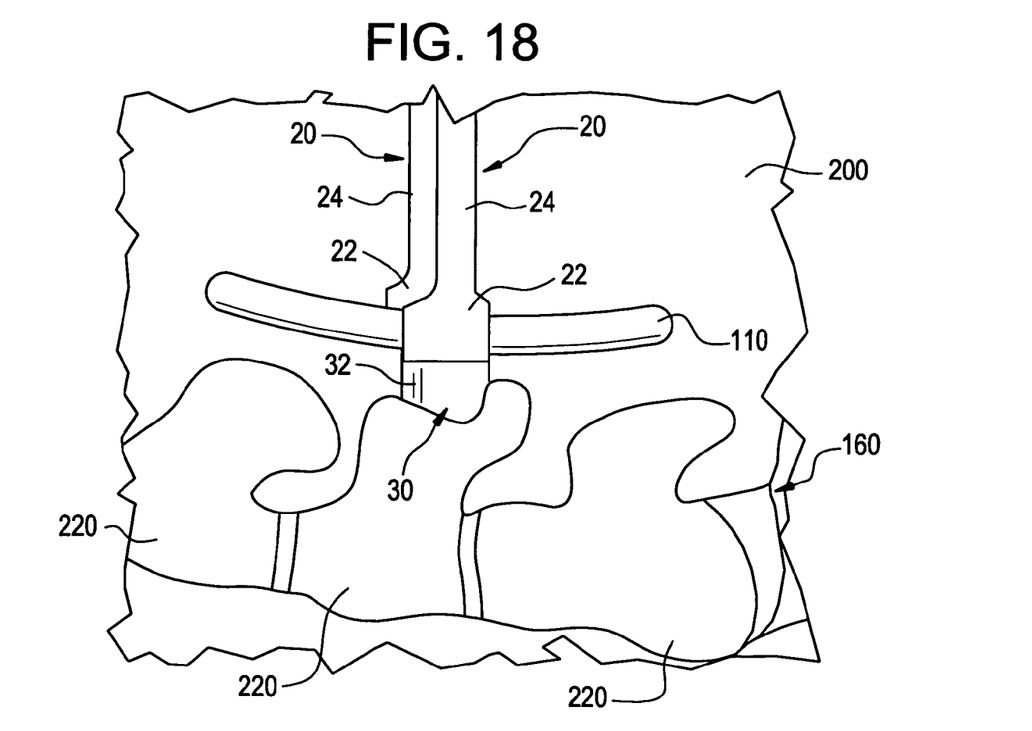
FIG. 18 is a perspective view of one embodiment of extenders, implant and bone anchor used in a surgical procedure.
Figure 19:
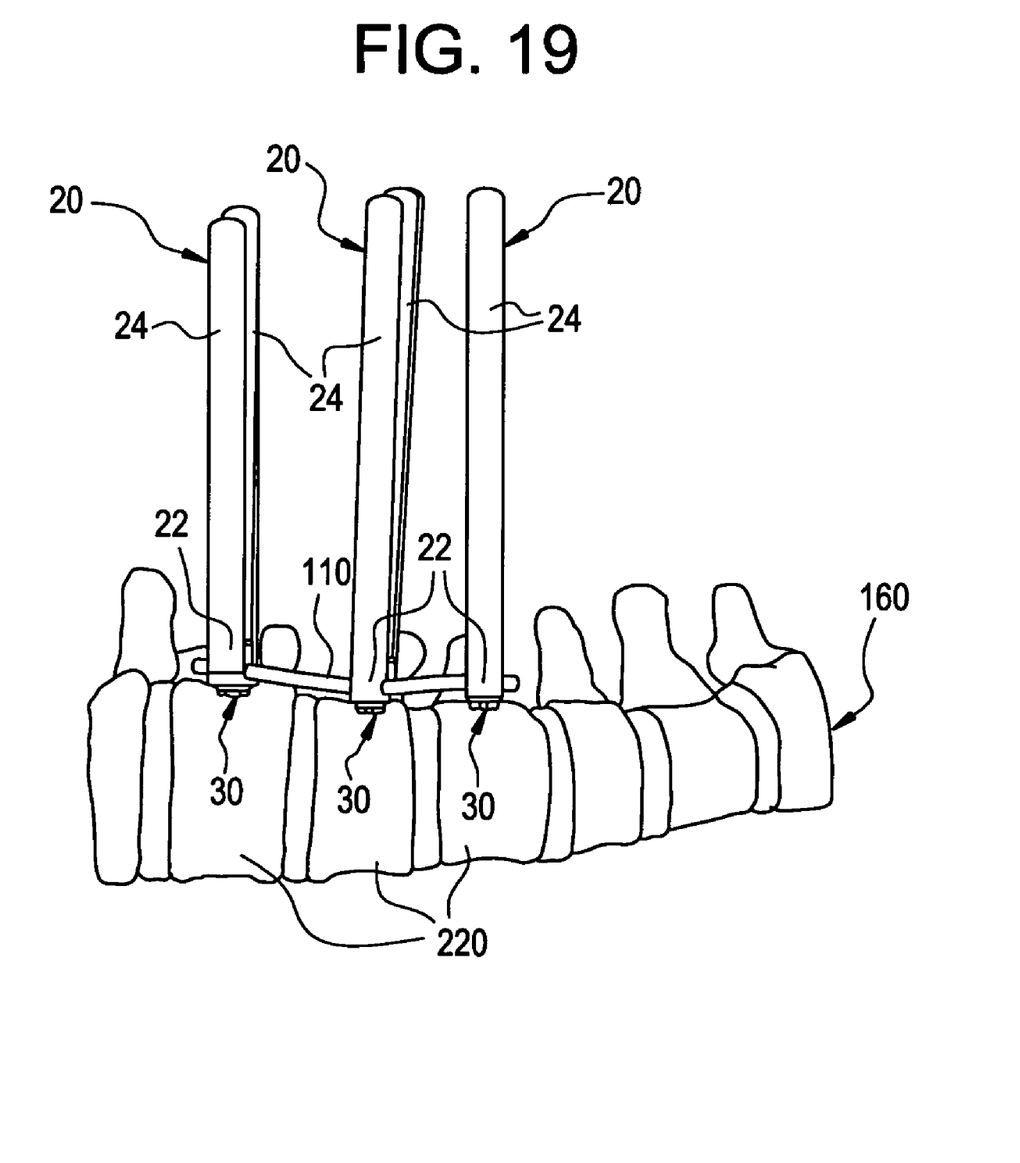
FIG. 19 is a perspective view of one embodiment of a plurality of extenders used in a surgical procedure.

In FIGS. 7-10, a driver 60 includes at least one retainer 62, a bit 66 and an end 64. In one embodiment, the driver 60 is used to insert the bone anchor 30 into a boney element of a patient. In this regard, the driver 60 comprises an internal mechanism or connection (not shown) to facilitate driving the bone anchor 30 into the boney element. In one embodiment, as shown in FIGS. 7 and 10, the driver 60 comprises a bit 66 that mates with a portion of the bone anchor 30 to drive the bone anchor into a boney element. In another embodiment, the portion of the bone anchor 30 that the bit 66 of the driver 60 mates with is a set screw 96 (FIG. 13). It should be appreciated that, in one embodiment, the set screw 96 (FIG. 13) is positionable in the center portion 100 (FIG. 2) of the head 32 of the bone anchor 30, and the set screw 96 (FIG. 13) is used to capture an implant 110 (FIG. 13) in the head 32 of the bone anchor 30. Further, in one embodiment, the set screw 96 (FIG. 13) is threadingly engageable with the head 32 of the bone anchor 30. In another embodiment, the bit 66 of the driver 60 engages the portion of the bone anchor 30 and rotates the bone anchor 30 to screw the bone anchor 30 in the boney element. In one embodiment, an internal mechanism (not shown) is used to connect the end 64 to the bit 66 such that movement of the end 64 also moves the bit 66. In another embodiment, an external driving device (not shown) connects to the end 64 to provide an externally powered force to move the end 64 and in turn move the bit 66 to drive the bone anchor 30 into the boney element. In one representative embodiment, the externally powered driving device can comprise a power drill. In one embodiment, the movement provided is a rotational force. In another embodiment, a handle (not shown) could be attached to the end 64 to allow a user to move the end 64 and thereby move the bit 66 of the driver 60 to drive the bone anchor 30 into a boney element. Similarly, in one embodiment, the movement of the handle could comprise a rotational or rotary force. It should be appreciated that the driver 60 can use mechanisms other than rotation to drive the bone anchor 30 into the boney element, such as, vertebral body 220 (FIGS. 16, 18 and 19). As further shown in FIG. 7-9, the extenders 20 can assist in holding or mounting the bone anchor 30 to the driver 60. To assist the holding or mounting, the driver 60 includes at least one retainer 62. As shown in FIG. 10, the retainer 62 comprises at least one slot 68 that is adapted to receive the elongated portion 24 of the extender 20. In one embodiment, the driver 60 includes two retainers 62 and each retainer 62 includes two separate slots 68 for holding the elongated portions 24 of the extenders 20. Further, the driver 60 slides down the extenders 20 via the slots 68 of the retainers 62 such that the bit 66 is placed in contact with the portion of the head 32 wherein the bone anchor 30 could be driven into the bone element. In addition, once the bone anchor 30 has been driven into the boney element, the driver 60 can be removed from the extenders 20 without having to remove the extenders 20 from the bone anchor 30. It should be appreciated that the bone anchor 30 could be attached to the extenders 20 before or after the elongated portions 24 of the extenders 20 have been inserted into the slots 68 of the retainers 62 on the driver 60. Further, it should further be appreciated that the retainer 62 can be securely connected to the driver 60 in a fixed orientation or the retainer 62 can be slidably connected to the driver such that the retainer 62 can slidably move along the length of the driver 60. The ability to have the extenders 20 hold or mount the bone anchor 30 with the driver 60 allows the extenders 20 to be in an advantageous position after the bone anchor 30 has been driven into the boney element such that the extenders 20 can be used to guide an implant to the surgical site after the driver 60 is removed from the extenders 20.

Figure 11:
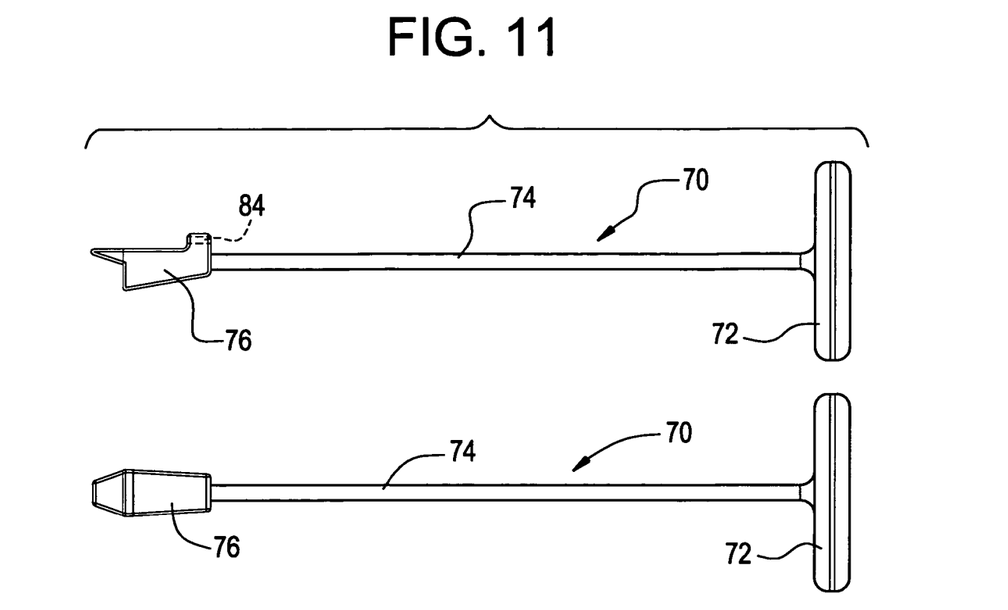
FIG. 11 is a front and side view of one embodiment of an extender remover tool.
Figure 12:
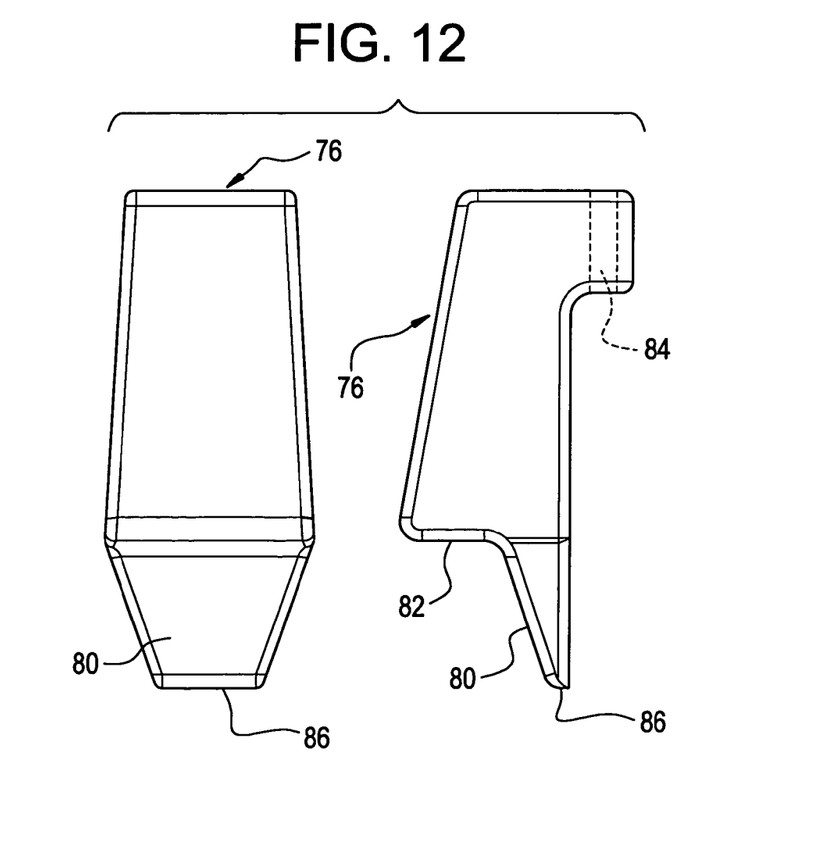
FIG. 12 is a front and side view of one embodiment of a head of an extender remover tool.

As shown in FIG. 2, the extenders 20 can be releasably attached to a bone anchor 30. In FIG. 11, one embodiment of a removal tool 70 includes a shaft 74 that is connected to a handle 72 and a wedge 76. In one embodiment, the handle 72 is connected to a first end of the shaft 74 and the wedge is connected to a second end of the shaft 74 wherein the first and second end are opposite from one another. It should be appreciated that, in one embodiment, the removal tool 70, shown in FIG. 11, can comprise a handle 72, shaft 74 and wedge 76 that are individual pieces that can be assembled together to form the removal tool 70. In another embodiment, the removal tool 70 includes a handle 72, shaft 74 and wedge 76 that are integrally formed from single piece that comprises the removal tool 70. Further, as shown in FIG. 11, the wedge 76 includes a slot 84 that accepts the elongated portion 24 of the extender 20. In use, after the extender 20 is releasably attached to the bone anchor 30, the removal tool 70 can be used to release the extender 20 from the bone anchor 30. The removal tool 70 is positioned such that the elongated portion 24 is inserted into the slot 84 of the wedge 76, and the removal tool 70 is slid down the elongated portion 24 of the extender 20. In this regard, to remove the extender 20 from the bone anchor 30, as the removal tool 70 is slid down the elongated portion 24, the removal tool 70 is moved such that the wedge 76 is located at an interface 78 (FIG. 2) where the extender 20 and the bone anchor 30 meet. Once the wedge 76 is located at the interface 78 (FIG. 2), a force is applied to handle 72. When the force is applied, the wedge 76 is pushed between the extender 20 and the bone anchor 30 whereby causing the side portions 46 of the clip 22 to release the clip 22 from the bone anchor 30. As such, once the clip 22 is released from the bone anchor 30 the extender 20 can be removed from the surgical site. Further, the slot 84 is sized to allow the thickness of the elongated portion 24 to pass through, but the thickness of the clip 22 is too large to pass through the slot 84. As such, since the clip 22 cannot pass through the slot 84, the extender 20 is easily retained in the removal tool 70 and can be easily removed from the surgical site together with the removal tool 70. As shown in FIGS. 12, the wedge 78 is advantageously shaped to conveniently remove the extender 20 from the bone anchor 30. In this regard, as shown in FIGS. 12, the wedge 76 includes a spike 80, shoulder 82 and a slot 84. As explained above, the slot 84 accepts the elongated portion 24 of the extender 20 to facilitate locating the wedge 76 to the interface 84 (FIG. 2) and for removal of the extender 20 after the extender 20 is released from the bone anchor 30. In one embodiment, as shown in FIG. 12, the wedge 76 also includes a spike 80 that is tapered on its sides. As shown in FIG. 12, the thickness of the spike 80 increases from end 86 to shoulder 82. The end 86 of the spike 80 is adapted to fit into the interface 78 (FIG. 2) between the extender 20 and the bone anchor 30. As mentioned above, the thickness of the spike 80 increases from the end 86 to the shoulder 82 such that as the spike 80 is inserted between the extender 20 and the bone anchor 30 a force is supplied to remove the clip 22 of the extender 20 from the bone anchor 30. It should be appreciated that once the removal tool 70 is placed in the interface 78 and a force is supplied to insert the removal tool 70 between the extender 20 and the bone anchor 30, the removal tool 70 can be moved or rocked to facilitate removal of the extender 20 from the bone anchor 30. In one embodiment, the wedge 76 also includes a shoulder 82 that can contact the head 32 of the bone anchor 30 after the wedge 76 of the removal tool 70 is inserted into the interface 78 (FIG. 2). The shoulder 82 can be used as a stop limit for the wedge 76 for providing a limit in which the spike 80 can be inserted into the interface 78 between the extender 20 and the bone anchor 30. Further, the shoulder 82 can also provide a bearing surface on which the wedge 76 of the removal tool 70 can be moved or rocked to facilitate inserting the spike 80 into the interface and/or in removing the extender 20 from the bone anchor 30.

Figure 14:
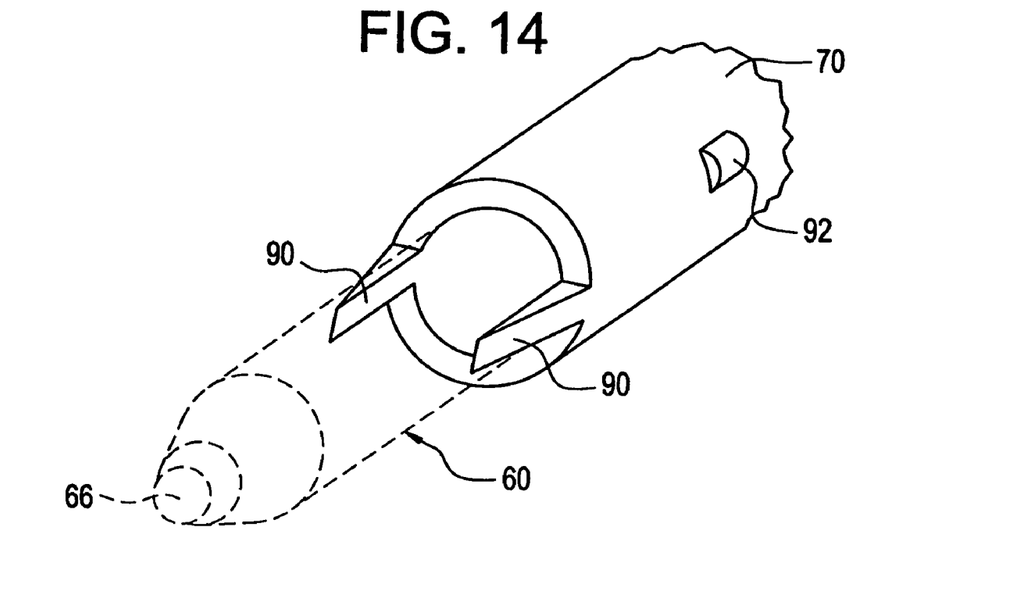
FIG. 14 is a perspective view of another embodiment of an extender remover tool.

In another embodiment as shown if FIGS. 13 and 14, a removal tool 70 includes tab 90 and capture 92. Further, the removal tool 70 comprises a cylindrical shape and can be hollow. The removal tool 70 has a tab 90 that is positionable in an interface 78 between the extender 20 and the bone anchor 30 to remove the extender 20 from the bone anchor 30. In this regard, the tab 90 can comprise a wedge shape to facilitate insertion into the interface 78. The removal tool 70 also includes capture 92 that is shaped to accept the elongated portion 24 of the extender 20. As such, once the elongated portion 24 is inserted into the capture the removal tool 70 can slide down the extender 20 and the tabs can be inserted in the interface 78. An external force can be supplied to the removal tool 70 to force the tab 90 into the interface 78 whereby removing the clip 22 of the extender 20 from the bone anchor 30. In another embodiment, two extenders 20 are releasably attached to a bone anchor 30. The removal tool 70, shown in FIGS. 13 and 14, includes two tabs 90 and at least two captures 92. The elongated potions 24 of each of the extenders 20 are inserted in a separate capture 92. The removal tool 70 is then slid down the elongated portions 24 such that each tab 90 is inserted in a separate interface 78 between an extender 20 and the bone anchor 30. An external force is supplied to the removal tool 70 to insert the respective tabs 90 into their respective interfaces 78 to simultaneously remove both the extenders 20 from the bone anchor 30. It should further be appreciated that, in one embodiment, the capture 92 is sized such that the elongated portion 24 is allowed to pass through while the wider clip portion 22 cannot pass through the capture 92. As such, when the extender 20 is released from the bone anchor 30, the removal tool 70 holds the extender 20 such that when the removal tool 70 is removed from the surgical site, the extender 20 is also taken out along with the removal tool 70.

Figure 15:
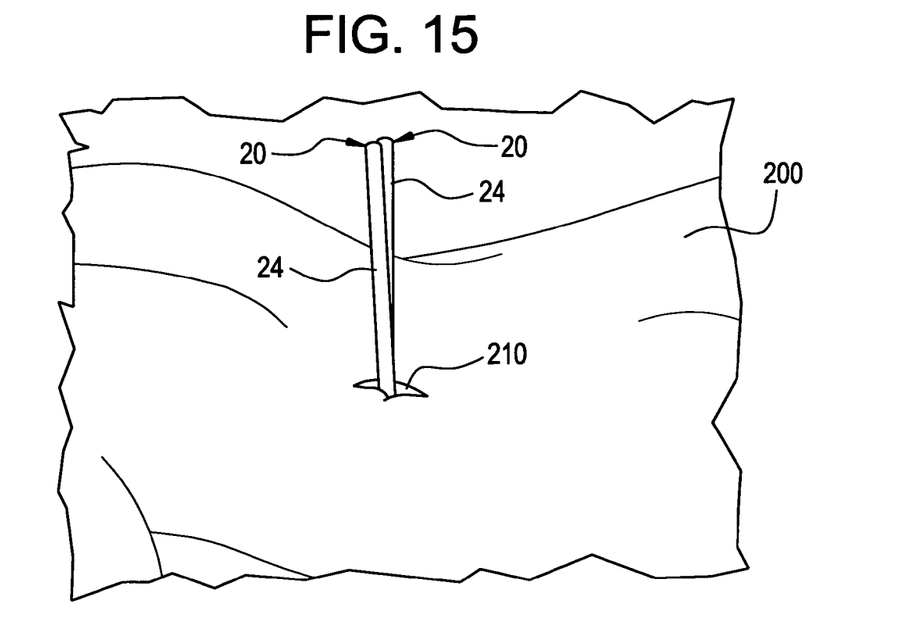
FIG. 15 is a perspective view of one embodiment of extenders used in a surgical procedure.
Figure 17:
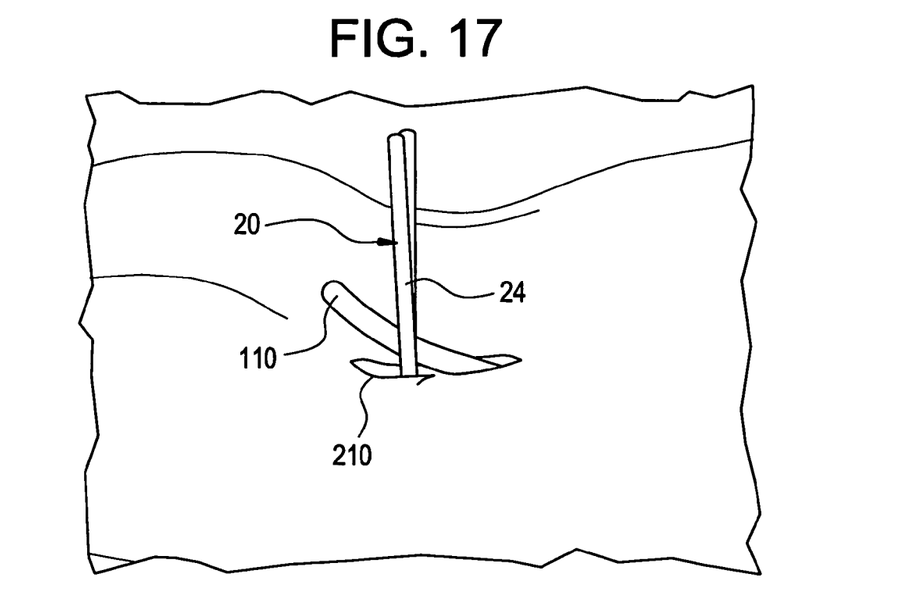
FIG. 17 is a perspective view of one embodiment of extenders and an implant used in a surgical procedure

As shown in FIGS. 15-19, the extender 20 can be used in a surgical procedure. Further, in one embodiment, the extenders 20 can be used in a spinal surgical procedure to assist in guiding an implant 110 to a spinal surgical site. As shown in FIGS. 15 and 16, at a surgical site 150, access to a vertebral body 220 of the spinal column 160 (FIG. 18) is provided through an incision 210 in a patient 200. As further shown in FIG. 16, the access is provided to the vertebral body 220 via a posterior approach to the patient 200. It should be appreciated that the extenders 20 can be used in other approaches to the patients, such as, an anterior approach, a lateral approach, and an anteriorlateral approach. Further, it should be appreciated that access can be provided to the vertebral body 220 using various surgical techniques, such as, minimal access surgical techniques, mini-open surgical techniques, open surgical techniques, percutaneous surgical techniques, other surgical techniques and/or various combinations thereof. In addition, in one embodiment, access to the vertebral body 220 is accomplished by using a set of cannulas that are sequentially inserted into the surgical site 150 to widen the surgical site 150. Also, in another embodiment, access can be provided to the vertebral body 220 using a retractor or speculum to open the surgical site 150. In yet another embodiment, access to the vertebral body 220 can be provided using an intermuscular retractor that is guided between the muscles of the patient to create the surgical site 150. A bone anchor 30 is inserted into the vertebral body 220. In one embodiment, as shown in FIG. 15, the bone anchor 30 is inserted into the pedicle 230 of the vertebral body 220. It should be appreciated that, in other embodiments, the bone anchor 30 can be inserted into other portions of the vertebral body 220, the spinal column 160 or other various bone elements of the patient 200. It should also be appreciated that the bone anchor 30 can be inserted into the vertebral body 220 using driver 60 (FIG. 7). At least one extender 20 is releasably attached to the head 32 of the bone anchor 30. It should be appreciated that in another embodiment, first and second extenders 20 can be attached to different portions of the head 32 of the bone anchor 30. The elongated portion 24 of the extender 20 extends longitudinally from the clip 22 to a point above the bone anchor 30. In addition, as shown in FIGS. 15-17, the elongated portion 24 extends to a point outside the patient 200. As shown in FIGS. 15, 17 and 18, the extenders 20 are used to define a pathway to guide an implant 110 from a point outside the patient to a surgical site 150 inside the patient and more specifically into the center portion 100 of the bone anchor 30. As further explained above, when using a single extender 20 per bone anchor 30, the single extender 20 per bone anchor 30 can also be used to guide the implant 110 from a point outside the patient to a surgical site 150 inside the patient. As shown in FIG. 15, when the extenders 20 are releasably attached to the bone anchor 30, the extenders 20 can be elastically deformed and/or bent to further open the incision 210 or the surgical site 150. In addition, when the extenders 20 are releasably attached to the bone anchor 30, the extenders 20 can be elastically deformed and/or bent to widen or open the pathway defined by the extenders 20 in which the implant 110 can travel. In even another embodiment, the extender 20 can be used in combination with various other medical instruments, such as, cannulas or retractors, used to open or widen the surgical site 150. As further shown in FIG. 13, once the implant 110 is guided to the center portion 100 of the bone anchor 30 a set screw 96 can be used to secure the implant 110 to the bone anchor 30. As shown in FIGS. 11-14, once the implant 110 is guided to the bone anchor 30 and before or after the implant 110 is secured to the bone anchor 30 using the set screw 96 (FIG. 13), the removal tool 70 can be used to remove the extenders 20 from the bone anchor 30. Further, the removal tool 70 and the extenders 20 are removed from the surgical site 150.

As further shown in FIG. 19, in even another embodiment, a plurality of bone anchors 30 and a plurality of extenders 20 can be used in a surgical procedure. As explained above, the bone anchors 30 are inserted into the vertebral bodies (V1, V2 and V3) 220. The extenders 20 can be releasably attached to the bone anchors 30 before or after insertion into the vertebral bodies 220. It should further be appreciated that, as explained above, a single extender 20 can be used per bone anchor 30. In another embodiment, extenders 20 may be attached to some specific bone anchors 30 and not attached to other specific bone anchors 30. The elongated portions 24 of the extenders 20 extend longitudinally from the clips 22 to a position above the bone anchors 30, and to a position outside the patient 200. The extenders 20 provide a pathway to guide the implant 110 from a position outside the patient 200 to a position inside the patient 200 and more specifically to a center portion 100 of the bone anchors 30. It should be appreciated that the implant 110 can comprise a rod or a series of rods. It should further be appreciated that the implant 110 can comprise implants other than rods, for example, flexible rods, polymeric rods, interbody devices, disc replacement implants, artificial disc implants or other surgical implants or devices. Once the implant 110 has been guided to the bone anchor 30 or the surgical site 150, the removal tool 70 can be used to release the extenders 20 from the bone anchor 30. After which, the removal tool 70 and the extenders 20 can be removed from the surgical site 150.

The foregoing discussion of the invention has been presented for purposes of illustration and description. Further, the description is not intended to limit the invention to the form disclosed herein. Consequently, variations and modifications commensurate with the above teachings and with the skill and knowledge of the relevant art are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A device for guiding surgical implants to a bone anchor during surgery comprising:
    a first bone anchor extender and a second bone anchor extender, wherein each of said first and second bone anchor extenders extends along a longitudinal axis between a proximal end and a distal end and further comprises:
        a clip positioned at said proximal end and including a medial portion extending along said longitudinal axis to said proximal end, said clip further including first and second side portions extending substantially parallel to said longitudinal axis and substantially perpendicularly to said medial portion, said first and second side portions each including a raised tab projecting therefrom toward the other said first and second side portions structured for receiving and releasably attaching to a first portion of a head portion of said bone anchor; and
        an extension portion extending distally from said clip to a position above said head portion of said bone anchor when said clip is releasably attached to said head portion of said bone anchor; and
    wherein said first and second bone anchor extenders assist in guiding the surgical implant to the bone anchor.

2. The device of claim 1 wherein said clip further comprises:
    a medial surface extending along said medial portion and from which said extension portion distally extends, said medial surface extending laterally between a first edge and an opposite second edge and further comprising a bumper projecting from said medial surface between said first and second side portions; and wherein said first side portion extends from said first edge of said medial surface and said second side portion extends from said second edge of said medial surface.

3. The device of claim 2 wherein said first side portion and said second side portion extend perpendicularly from said medial surface.

4. The device of claim 2 wherein said first side portion and said second side portion extend substantially perpendicularly from said medial surface.

5. The device of claim 2 wherein said raised tabs are located in facing relation to one another with each spaced a same distance from said medial surface and a same distance from said proximal end.

6. The device of claim 5 wherein said first raised tab is integrally formed with said first side portion and said second raised tab is integrally formed with said second side portion.

7. The device of claim 5 wherein each of said first raised tab and said second raised tab comprises an angled face and a retention edge, said retention edge being positioned opposite from said angled face and closer to said medial surface than said angled face.

8. The device of claim 7 wherein said angled face guides a portion of said head portion of said bone anchor to a position where said portion of said head portion is secured between said retention edge and said medial surface whereby retaining said bone anchor extension on said bone anchor.

9. The device of claim 5, wherein said first raised tab and said second raised tab are positioned in a plane spaced apart from and extending substantially parallel to said medial surface.

10. A device for guiding a surgical implant to a bone anchor during surgery comprising:

a first bone anchor extender extending along a longitudinal axis between a proximal end and a distal end, said first bone anchor extender further comprising a clip portion releasably attachable to said bone anchor, said clip portion extending from said proximal end toward said distal end of said first bone anchor extender and including a medial surface laterally extending between a first longitudinal sidewall and a second longitudinal sidewall, said first and second sidewalls extending substantially transversely from said medial surface to a terminal portion and forming facing surfaces defining an area therebetween for receiving said bone anchor, wherein said first bone anchor extender further comprises an elongate extension portion extending distally from said proximal portion to said distal end, said extension portion being bendable relative to said clip portion and elastic to revert back its pre-bent shape; and a second bone anchor extender extending along a longitudinal axis between a proximal end and a distal end, said second bone anchor extender further comprising a clip portion releasably attachable to said bone anchor on a side of said bone anchor opposite said first bone anchor extender, said clip portion extending from said proximal end toward said distal end of said second bone anchor extender and including a medial surface laterally extending between a first longitudinal sidewall and a second longitudinal sidewall, said first and second sidewalls extending substantially transversely from said medial surface to a terminal portion and forming facing surfaces defining an area therebetween for receiving said bone anchor, wherein said second bone anchor extender further comprises an elongate extension portion extending distally from said proximal portion to said distal end, said extension portion being bendable relative to said clip portion and elastic to revert back its pre-bent shape, wherein said extension portions of said first and second bone anchor extenders are spaced from one another to provide a pathway therebetween.

11. The device of claim 10 wherein said first and second bone anchor extenders each further comprises:

said extension portion extending distally from a distal end of said clip portion to a position above said bone anchor when said clip portion is releasably attached to said bone anchor.

12. The device of claim 11 wherein for each of said first and second bone anchor extenders a width of said clip portion is greater than a width of said extension portion.

13. The device of claim 11 wherein for each of said first and second bone anchor extenders each of said first sidewall and said second sidewall includes a tapered portion extending between said terminal portion and said extension portion at said distal end of said clip portion.

14. The device of claim 10 wherein for each of said first and second bone anchor extenders said area defined between said first and second sidewalls is sized and structured for receiving a portion of a head portion of said bone anchor.

15. The device of claim 14 wherein for each of said first wad second bone anchor extenders said medial surface is contoured complementarily to said head portion of said bone anchor.

16. The device of claim 15 wherein said medial surface is contoured in an arc.

17. The device of claim 10 wherein for each of said first and second bone anchor extenders said first sidewall and said second sidewall extend substantially parallel to one another in a first direction from said medial surface.

18. The device of claim 10 wherein for each of said first and second bone anchor extenders said medial surface further comprises a bumper extending transversely therefrom, said bumper being positioned to space said bone anchor from said medial surface when said bone anchor extender is connected to said bone anchor.

19. The device of claim 18 wherein said bumper is integrally formed with said medial surface.

20. A device for guiding a surgical implant to a bone anchor during surgery comprising:

a first bone anchor extender extending along a longitudinal axis between a proximal end and a distal end, said first bone anchor extender further comprising a clip portion releasably attachable to said bone anchor, said clip portion extending from said proximal end toward said distal end of said first bone anchor extender and including a medial surface laterally extending between a first longitudinal sidewall and a second longitudinal sidewall, said first and second sidewalls extending substantially transversely from said medial surface to a terminal portion and forming facing surfaces defining an area therebetween for receiving said bone anchor; and a second bone anchor extender extending along a longitudinal axis between a proximal end and a distal end, said second bone anchor extender further comprising a clip portion releasably attachable to said bone anchor on a side of said bone anchor opposite said first bone anchor extender, said clip portion extending from said proximal end toward said distal end of said second bone anchor extender and including a medial surface laterally extending between a first longitudinal sidewall and a second longitudinal sidewall, said first and second sidewalls extending substantially transversely from said medial surface to a terminal portion and forming facing surfaces defining an area therebetween for receiving said bone anchor, wherein for each of said first and second bone anchor extenders said first sidewall further comprises a first raised tab positioned thereon and said second sidewall further comprises a second raised tab positioned thereon.

21. The device of claim 20 wherein said first raised tab is integrally formed with said first sidewall and said second raised tab is integrally formed with said second sidewall.

22. The device of claim 20 wherein each of said first raised tab and said second raised tab comprises an angled face and a retention edge, said retention edge being positioned opposite from said angled face and closer to said medial portion than said angled face.

23. The device of claim 22 wherein said angled face guides a portion of a head portion of said bone anchor to a position where said portion of said head portion is secured between said retention edge and said medial surface whereby retaining said bone anchor extension on said bone anchor.

24. The device of claim 20, wherein for each of said first and second bone anchor extenders said first raised tab is positioned between said terminal portion of said first sidewall and said medial surface and said second raised tab is positioned between said terminal portion of said second sidewall and said medial surface.

25. The device of claim 24, wherein for each of said first and second bone anchor extenders said first and second raised tabs are elongated and extend substantially parallel to said longitudinal axis of said bone anchor extender.

26. The device of claim 25, wherein for each of said first and second bone anchor extenders said first raised tab further includes a first leading edge extending at an angle from said first sidewall toward said medial surface and intersecting a first retention edge extending substantially transversely from said first sidewall and said second raised tab further includes a second leading edge extending at angle from said second sidewall toward said medial surface and intersecting a second retention edge extending substantially transversely from said second sidewall.

27. The device of claim 26, wherein for each of said first and second bone anchor extenders said clip portion further comprises a projection positioned on said medial surface between said first and second sidewalls, said projection extending transversely from said medial surface and being structured to space said bone anchor from said medial surface and into contact wit said first and second retention edges when said clip portion is releasably attached to said bone anchor.

28. A device for guiding a surgical implant to a bone anchor during surgery, said device comprising:

an elongated guide member extending along a longitudinal axis between a proximal end and a distal end, said elongated member defining a clip portion at said proximal end, said clip portion including:
- a recessed medial surface extending between a first raised lateral edge and a second raised lateral edge, said first and second raised lateral edges each extending substantially perpendicularly to said medial surface and said medial surface includes a bumper extending therefrom between said first and second raised lateral edges;
- a first elongated tab portion projecting substantially transversely from said first lateral edge toward said second lateral edge; and
- a second elongated tab portion projecting substantially transversely from said second lateral edge toward said first lateral edge; and wherein said clip portion is structured to receive a portion of said bone anchor between said first and second elongated tab portions and said medial surface to releasably attach said guide member to said bone anchor.

* * * * *